(12) United States Patent
Doona et al.

(10) Patent No.: US 11,358,863 B2
(45) Date of Patent: Jun. 14, 2022

(54) METHOD AND COMPOSITION OF HUMIDITY-CONTROLLED GENERATION OF CHLORINE DIOXIDE IN POLYMERS AND SUPERABSORBENT HYDROGELS

(71) Applicant: BRANDEIS UNIVERSITY, Waltham, MA (US)

(72) Inventors: Christopher J. Doona, Marlborough, MA (US); Florence E. Feeherry, Natick, MA (US); Kenneth Kustin, Chapel Hill, NC (US); Irving R. Epstein, Newton, MA (US)

(73) Assignee: Brandeis University, Waltham, MA (US)

( * ) Notice: Subject to any disclaimer, the term of this patent is extended or adjusted under 35 U.S.C. 154(b) by 129 days.

(21) Appl. No.: 16/776,789

(22) Filed: Jan. 30, 2020

(65) Prior Publication Data

US 2020/0239306 A1    Jul. 30, 2020

Related U.S. Application Data

(62) Division of application No. 15/822,528, filed on Nov. 27, 2017, now Pat. No. 10,626,016.

(51) Int. Cl.

| | |
|---|---|
| *C01B 11/02* | (2006.01) |
| *A01N 59/00* | (2006.01) |
| *A01N 35/02* | (2006.01) |
| *A01N 25/10* | (2006.01) |
| *A01N 25/04* | (2006.01) |
| *A61L 15/60* | (2006.01) |
| *A61L 2/20* | (2006.01) |
| *A61L 15/24* | (2006.01) |
| *A61L 15/28* | (2006.01) |
| *A61L 15/18* | (2006.01) |
| *A61L 15/20* | (2006.01) |
| *A61L 2/00* | (2006.01) |
| *A61L 15/46* | (2006.01) |

(52) U.S. Cl.
CPC ............ *C01B 11/024* (2013.01); *A01N 25/04* (2013.01); *A01N 25/10* (2013.01); *A01N 35/02* (2013.01); *A01N 59/00* (2013.01); *A61L 2/0094* (2013.01); *A61L 2/20* (2013.01); *A61L 15/18* (2013.01); *A61L 15/20* (2013.01); *A61L 15/24* (2013.01); *A61L 15/28* (2013.01); *A61L 15/46* (2013.01); *A61L 15/60* (2013.01)

(58) Field of Classification Search
CPC ....... C01B 11/024; A01N 59/00; A01N 35/02; A01N 25/10; A01N 25/04; A61L 15/60; A61L 15/46; A61L 15/24; A61L 15/28; A61L 15/18; A61L 15/20; A61L 2/20; A61L 2/0094; A61L 2300/106; A61L 2300/404; A61L 2300/10
See application file for complete search history.

(56) References Cited

U.S. PATENT DOCUMENTS

| | | |
|---|---|---|
| 3,591,515 A | 7/1971 | Lovely |
| 4,081,520 A | 3/1978 | Swindells et al. |
| 4,473,540 A | 9/1984 | Fredette |
| 4,504,442 A | 3/1985 | Rosenblatt et al. |
| 4,681,739 A | 7/1987 | Rosenblatt et al. |
| 4,908,188 A | 3/1990 | Jefferis, III et al. |
| 5,234,678 A | 8/1993 | Rosenblatt et al. |
| 5,407,656 A | 4/1995 | Roozdar |
| 5,507,867 A | 4/1996 | Ruggiero et al. |
| 5,770,171 A | 6/1998 | Sundblad et al. |
| 7,048,842 B2 | 5/2006 | Tremblay et al. |
| 7,220,367 B2 | 5/2007 | Speronello et al. |
| 7,261,821 B2 | 8/2007 | Beardwood |
| 7,504,074 B2 | 3/2009 | Martens et al. |
| 7,534,398 B2 | 5/2009 | Dee et al. |
| 7,625,533 B2 | 12/2009 | Doona et al. |
| 7,883,640 B2 | 2/2011 | Doona et al. |
| 9,382,116 B2 | 7/2016 | Isaac et al. |
| 9,517,934 B2 | 12/2016 | Doona et al. |
| 2008/0076855 A1* | 3/2008 | Reif ................... C09J 111/02 524/71 |

(Continued)

FOREIGN PATENT DOCUMENTS

| | | |
|---|---|---|
| EP | 0604676 B1 | 7/1994 |
| EP | 2962988 A1 | 1/2016 |
| WO | 0215855 A1 | 2/2002 |

OTHER PUBLICATIONS

Horvath et al., Kinetics and Mechanism of the Decomposition of Chlorous Acid, Journal of Physical Chemistry A, 2003, 107:6966-6973.

(Continued)

*Primary Examiner* — Andrew J. Oyer
(74) *Attorney, Agent, or Firm* — Quarles & Brady LLP

(57) ABSTRACT

A composition and method for chlorine dioxide production through reaction-diffusion chemistry that facilitates the in situ generation of chlorine dioxide, wherein a dry solid composition of hydroxymethanesulfinic acid monosodium salt dihydrate (abbreviated HMS) and a chlorine dioxide precursor are activated via the addition or absorption of water to produce chlorine dioxide. The dry solid chemical composition comprises dry, safe, transportable reagents that integrate with polymeric materials such as packaging and superabsorbent and stimuli-responsive hydrogel polymers to combine with water to produce chlorine dioxide.

19 Claims, No Drawings

(56) References Cited

U.S. PATENT DOCUMENTS

2016/0068393 A1* 3/2016 Doona ............... C01B 11/024
 423/477

OTHER PUBLICATIONS

Lehtimaa et al., Reactions and Kinetics of Cl(III) Decomposition, Industrial & Engineering Chemistry Research, 2008, 4:5284-5290.
Ray et al., Development of Chlorine Dioxide Releasing Film and Its Application in Decontaminating Fresh Produce, Journal of Food Science, 2013, 78(2):M276-M284.
Salem et al., Oxyhalogen-Sulfur Chemistry: Oxidation of Hydroxymethanesulfinic Acid by Chlorite, Journal of Physical Chemistry, 1996, 100:9377-9384.

* cited by examiner

METHOD AND COMPOSITION OF HUMIDITY-CONTROLLED GENERATION OF CHLORINE DIOXIDE IN POLYMERS AND SUPERABSORBENT HYDROGELS

CROSS-REFERENCE TO RELATED APPLICATIONS

This application is a divisional of U.S. patent application Ser. No. 15/822,528, filed Nov. 27, 2017, which is incorporated by reference in its entirety.

STATEMENT REGARDING FEDERALLY SPONSORED RESEARCH

The invention described herein may be manufactured and used by the U.S. Government for governmental purposes without the payment of any royalty thereon.

BACKGROUND OF THE INVENTION

1. Field of the Invention

The present disclosure generally relates to methods, processes, chemical reactions, or mixed-chemical technologies for the generation of chlorine dioxide. More particularly, the present disclosure relates to a composition and to a method of humidity-controlled generation of chlorine dioxide in polymers, superabsorbent hydrogels, stimuli-responsive hydrogels, smart materials, and polymeric packaging films.

2. Description of Related Art

Chlorine dioxide is a well-known bleaching agent for paper pulp or flour and is also a well-known biocidal or anti-microbial agent for a broad spectrum of microorganisms in decontamination applications for bacterial spores, vegetative pathogens, viruses, phage, and fungi and molds. Millions of pounds of chlorine dioxide are produced for use in these industrial and technological settings. Large-scale methods for chlorine dioxide production employ the reduction of chlorate in concentrated mineral acid solutions of high normality.

As a decontaminant, it has been widely used for its efficacy, material compatibility, and safety for both users and the environment. However, because of the hazards associated with the condensed phase as a high concentration liquid or solution, chlorine dioxide cannot be pre-generated, then shipped or transported in trucks or other vehicles to distant locations. Rather, it must be generated on-site, at point-of-use, and at-will for use in sanitation, disinfection, chemical decontamination, biological decontamination, and other anti-microbial applications.

There are many documented methods for chlorine dioxide generation. For example, Doona et al. (U.S. Pat. Nos. 7,625,533 and 7,883,640) teach chlorine dioxide {$ClO_2$, oxidation state [Cl(IV)]} production by exothermic effector-driven chemical reactions involving oxidizing sodium chlorite ion through the addition of a chemical reductant and a unique chemical effector in water or aqueous solution. In contradistinction to the art of this unique effector chemistry, previous prior art uses chemical oxidants, or acids for acidification to convert chlorite ion {$ClO_2^-$, oxidation state [Cl(III)]} to chlorine dioxide. The effector-driven chemical reaction of U.S. Pat. Nos. 7,625,533 and 7,883,640 generates reactive intermediates through reduction that are actually the entities responsible for chemically oxidizing chlorite ion [Cl(III)] to chlorine dioxide [Cl(IV)]. Certain reductants with special chemical properties and reactivities can convert chlorite ion to chlorine dioxide in water or aqueous solution without requiring a chemical effector or significant exothermic heat production. One such reductant, for example, is formamidinesulfinic acid or its conjugate base (abbreviated FSA, U.S. Pat. No. 9,517,934), which is hereby incorporated herein by reference. The chlorine dioxide produced by all of these prior art chemical systems, whether in solution phase or in the gaseous state, can subsequently be used in myriad practical anti-microbial applications for the inactivation of bacterial cells and spores, fungi, molds, mildew, viruses, and bacteriophage, or for chemical decontamination.

As an alternative method of generation, the continuous reduction of sodium chlorate in high acid (supra) can be carried out in homogeneous chemical or electrochemical reactors. Reductants often include methanol, sulfur dioxide, hydrogen peroxide, and chloride ion. These and other standard processes are described in handbooks and encyclopedias of chemical technology; e.g., Vogt et al., "Ullmann's Encyclopedia of Industrial Chemistry." The chief reductant is methanol (Sundblad et al., U.S. Pat. No. 5,770,171 and Fredette, U.S. Pat. No. 4,473,540). Automation of the reduction process is taught by Swindells et al. (U.S. Pat. No. 4,081,520).

Arguably the most common high volume oxidation technology involves using chlorine as dichlorine gas or as hypochlorite to oxidize chlorite ion to chlorine dioxide. Refinement of the oxidation process incorporates automatic monitoring as taught by Beardwood (U.S. Pat. No. 7,261,821) and Martens et al. (U.S. Pat. No. 7,504,074). Problems with this method of chlorine dioxide production are detailed by Jefferis, III et al. (U.S. Pat. No. 4,908,188). Jefferis, III et al. teaches the extreme corrosivity of dichlorine gas and its hydrolysis products, and the necessity of preventing accidents and ensuring safety. An attempt was made to reduce the inherent danger of dichlorine oxidation by diluting the gas with carbon dioxide (Rosenblatt et al., U.S. Pat. No. 5,234,678).

Producing chlorine dioxide by chlorate ion reduction in high acid and by dichlorine gas oxidation are processes most suited to controlled, less populated industrial settings. They are less well suited for smaller-scale, more populated environments such as kitchens, hospital rooms, rest rooms, class rooms, homes, boats or recreational vehicles, because all of the reactants and reaction byproducts are often considered too dangerous, corrosive and environmentally hazardous to be used in such domestic, consumer-friendly environments. Methods to circumvent these problems for smaller-scale environments have therefore been developed.

One method for avoiding the dangers of dichlorine gas utilizes its hypochlorite ion hydrolysis product (Aalves, European Pat. App. No. EP 2,962,988). This method is complex and necessitates multiple additions of citric acid to initiate reaction, and the addition of sodium bicarbonate to control pH. As taught by Rosenblatt et al. (U.S. Pat. Nos. 4,504,442 and 4,681,739), persulfate can oxidize chlorite ion to chlorine dioxide. However, this reaction is relatively slow. One of skill in the art would also recognize that it is not necessary to use a chemical oxidant, as an electrolysis cell can accomplish the oxidation. Tremblay et al. (U.S. Pat. No. 7,048,842) teach the use of a porous anode to effect the electrochemical oxidation. Unfortunately, this method requires power and is a highly inefficient process. Because of these inherent difficulties, resort has very frequently been made to acidification of sodium chlorite solutions.

Acidification of sodium chlorite solutions at a pH of 2 or below produces chlorine dioxide gas in a reasonably short period of time due to disproportionation of hypochlorous acid. Many researchers have studied the stoichiometry and kinetics of this disproportionation reaction, which is invariant to the identity of the molecules that provide the proton ions to induce a pH below 2. One such study examines all possible intermediates (Horvath et al., *J. Phys. Chem. A* 2003, 107, 6966-6973); a second, more limited study eliminates hypochlorite ion as an intermediate by scavenging it with dimethyl sulfoxide (Lehtimaa et al. *Ind. Eng. Chem. Res.* 2008, 47, 5284-5290). When chlorine dioxide is generated in this manner, the need for concentrated acids, including their transportation, storage, and handling, and the need to dispose of acid hazardous waste, makes technologies based on this reaction chemistry unsuited for use in the high-intensity, rapid-mobility environments characteristic of far-forward military deployments.

The main emphasis of early acidification technology was focused on speeding up the reaction. Utilizing pre-mixed reagents such as sodium chlorite and iron(III) chloride adsorbed on solids has been shown to result in very slow chlorine dioxide release upon addition of liquid water (Lovely, U.S. Pat. No. 3,591,515). Eliminating the adsorbent materials allows the reaction to proceed more rapidly, but necessitates segregation of the two reagents prior to mixing with water. Reactive precursors to a desired chemical reaction can be segregated by barriers well known in the chemical and chemical engineering arts, such as valves or membranes. For example, Roozdar (U.S. Pat. No. 5,407,656) teaches dissolution of precursors in solution or in gel form in separate vessels followed by mixing after opening appropriate valves. Dee et al. (U.S. Pat. No. 7,534,398) teaches the sequestration of reactants in packets made of membrane material that dissolves in water, whereupon the reactants are allowed to mix and react.

For the generation of chlorine dioxide, the traditional prior art teaches the reduction of chlorate ion, oxidation of chlorite ion, or the disproportionation of chlorous acid. These methods are superseded in terms of chemical control, reduced hazards, convenience, and safety to users and the environment by the more recent and technologically advanced methods involving transient reactive intermediates (TRI). The earliest TRI methods teach the reduction of chlorite in the presence of an effector to produce fast-acting intermediates which invoke complex reaction chemistry to generate chlorine dioxide and heat (U.S. Pat. Nos. 7,625,533 and 7,883,640, previously cited above). The inherent reaction chemistry of this type of approach has been explained in detail in Doona et al. (U.S. Pat. No. 9,517,934) for a reaction that does not require an effector, namely, the chemical reaction between FSA and chlorite.

In view of the deficiencies of the above prior art, there is a current need for a composition and/or method for generating chlorine dioxide without the use of corrosive acids or buffers to regulate pH. Additionally, any composition and/or method that could controllably produce different amounts of chlorine dioxide from dry, safe, lightweight, transportable reagents or without the addition of energy or need for specialized equipment would provide a significant advantage over the prior art.

SUMMARY OF THE INVENTION

The present disclosure overcomes the aforementioned drawbacks by providing a composition and method for chlorine dioxide production through reaction-diffusion chemistry that facilitates the in situ generation of chlorine dioxide, wherein a dry solid composition of hydroxymethanesulfinic acid monosodium salt dihydrate (abbreviated HMS) and a chlorine dioxide precursor are activated via the addition or absorption of water to produce chlorine dioxide. As used herein, hydroxymethanesulfinic acid monosodium salt dihydrate with the abbreviation HMS comprises the commercially available monosodium salt and includes all of the acid or base species conjugates that arise from the dissolution of HMS in water and the equilibration of HMS in water, with relative proportions of these species depending on the pH of the aqueous solution so produced. All of the HMS species can participate in the chemical reaction with the precursor to produce chlorine dioxide. The HMS utilized in the present invention is readily available commercially, has the registered chemical number (CAS Number 6035-47-8), and is also known by its common name rongalite.

It is therefore an advantage of the present disclosure to provide a chemical composition comprising dry, safe, transportable reagents that combine with water to produce chlorine dioxide. This composition is lightweight and energy-independent. It does not require the use of difficult-to-transport, exogenously-powered equipment in austere environments, remote areas, or far-forward deployments, where rapid mobility is needed. The instant invention does not require the addition of corrosive acids, acid protons, a chemical effector, or other hazardous reagents such as chlorate or pressurized cylinders of dichlorine gas. The starting materials of this reaction are benign and the reaction end-products are inert, such that they are safe to users and the environment and can be disposed of safely and conveniently without special handling. The HMS-chlorine dioxide precursor reaction is relatively non-exothermic compared with the prior art.

In an aspect, the present disclosure provides a dry solid composition. The dry solid composition can be used for generating chlorine dioxide. The composition includes a chlorine dioxide precursor and HMS. The chlorine dioxide precursor and HMS are physically arranged such that contacting one or both with a fluid containing water produces chlorine dioxide.

In another aspect, the present disclosure provides a method for generating chlorine dioxide. The method includes contacting a dry solid composition with a fluid containing water. The dry solid composition includes a chlorine dioxide precursor and HMS. The contact produces the chlorine dioxide.

In a further aspect, the present disclosure provides a method of making a dry solid composition. The method includes physically arranging a chlorine dioxide precursor and HMS in an anhydrous environment. The physically arranging is such that contacting the chlorine dioxide precursor, the HMS, or both with a fluid containing water produces chlorine dioxide.

The foregoing and other aspects and advantages of the invention will become apparent through the following description.

DETAILED DESCRIPTION OF THE INVENTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in a non-exclusive manner, so the referenced elements, components, or steps may be combined with other elements, components, or steps that are not expressly referenced. Embodiments referenced as "comprising", "including", or "having" certain elements are also contemplated as "consisting essentially of" and "consisting of" those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive of their endpoints. For example, a numeric range of between 1 and 10 includes the values 1 and 10. When a series of numeric ranges are disclosed for a given value, the present disclosure expressly contemplates ranges including all combinations of the upper and lower bounds of those ranges. For example, a numeric range of between 1 and 10 or between 2 and 9 is intended to include the numeric ranges of between 1 and 9 and between 2 and 10.

The present disclosure provides a dry solid composition for generating chlorine dioxide. The composition comprises a chlorine dioxide precursor and HMS. In some cases, the composition consists essentially of the chlorine dioxide precursor and the HMS. In some cases, the composition consists of the chlorine dioxide precursor and the HMS. The chlorine dioxide precursor and HMS are physically arranged such that contacting one or both with a fluid containing water produces the chlorine dioxide. The dry solid composition may be in the form of a powder or crystals.

The molar concentration ratio of the chlorine dioxide precursor to the HMS may be between 100:1 and 1:100, including but not limited to, between 5:1 and 1:5 or between 2:1 and 1:2. The chlorine dioxide precursor may be present in an amount by weight of between 1% and 99%, including but not limited to, between 10% and 90%, between 25% and 75%, between 40% and 60%, between 15% and 35%, between 60% and 85%, between 20% and 50%, or between 50% and 70%. The HMS may be present in an amount by weight of between 1% and 99%, including but not limited to, between 10% and 90%, between 25% and 75%, between 40% and 60%, between 15% and 35%, between 60% and 85%, between 20% and 50%, or between 50% and 70%.

The chlorine dioxide precursor may be a chlorite ion salt. The chlorine dioxide precursor may be sodium chlorite. Other chlorite salts in which the positively charged counterion can be chosen from any available cation, such as lithium, potassium, calcium, aluminum, or ammonium ion may be used. Similarly, the purity or grade of the chlorite salt can be selected from Technical Grade (80%) to an analytical reagent (≥99%) without changing the essence of the instant invention.

The chlorine dioxide precursor and the HMS may be spatially separated from one another.

A material can comprise the composition described above. The composition may be integrated into and/or onto the material. The material may be selected from the group consisting of a polymeric material, a woven textile, a non-woven textile, a metallic material, a ceramic material, a crystalline material, and combinations thereof. The composition may be located on a surface of the material. The material may comprise at least a portion of a sanitary garment, a shelter, a clothing item, a hat, a helmet, a uniform, a footwear item, a piece of wearable protective equipment, or a combination thereof. For wearable items, the chlorine dioxide generation may reduce incidences of odors, rashes, irritations, and infections that occur when uniforms/clothing are worn without access to laundries or showers for prolonged periods.

The above material comprising the composition may be the polymeric material. The polymeric material can be a hydrogel. As used herein, a hydrogel refers to a 3-D network of polymer chains that are usually made of hydrophilic natural or synthetic polymers with covalent bonds, hydrogen bonds, ionic bonds, and hydrophobic interactions connecting the polymer chains together. Hydrogels, such as cellulose acetate for example, are superabsorbent materials that can absorb water in their 3-D networks and swell, but can also remain insoluble in water. The hydrogel may be a stimuli-responsive hydrogel, also called a smart material. As used herein, a stimuli-responsive hydrogel or smart material refers to a hydrogel polymeric network that is capable of undergoing reversible changes in properties in response to changes in environmental stimulus, such as absorbing water at low temperatures and releasing water at high temperatures due to changes in the polymeric structure occurring with appropriate changes in temperature. Stimuli-responsive hydrogels can respond to changes in stimuli relating to solvent composition, temperature, pH, electricity, magnetic field, moisture/water, light, and/or electromagnetic radiation. The stimuli-responsive hydrogel may comprise at least one of poly-{N-isopropylacrylamide}, poly-{N-isopropylacrylamide-co-chitosan}, or poly-{N-isopropylacrylamide-co-acrylic acid}. The polymeric material may be polymers commonly used in industrial packaging, such as polyethylene or polyethyleneterephthalate, or petroleum-based plastics such as polypropylene, polyvinylchloride, or polystyrene. The polymeric material may also be biodegradeable films obtained from bio-polymers, such as bio-derived monomers (polylactic acid) or films from bio-mass (cellulose, starch, gelatin) or microbes (polyhydroxyalkanoate), or any other polymer commonly used in packaging.

The present disclosure also provides for a method for generating chlorine dioxide. The method comprises contacting a dry solid composition comprising a chlorine dioxide precursor and HMS with a fluid containing water. Contacting the composition with the fluid produces chlorine dioxide.

The fluid containing water may be a gas comprising water vapor. The gas comprising water vapor can be at a relative humidity (RH) of 1-100%, preferably ≥80% RH. RH is the standard measure of humidity, which can also be expressed as water activity ($a_w$), water vapor partial pressure, or the thermodynamic entity chemical potential without changing its meaning. The method may further comprise controlling the RH in a distinct atmosphere such as an enclosure or confined space such as to regulate the production of chlorine dioxide.

The fluid containing water may be a human secretion. For example, the fluid may be perspiration, urine, or feces. The fluid containing water may also be produced from transpiring or respiring produce. For example, the fluid may be produced from fruits, vegetables, cut flowers, or any other plant.

The method discussed above may be used to decontaminate an item or a plurality of items. The decontamination method can include the chlorine dioxide generation described above and further comprise contacting the item with the chlorine dioxide produced using the above method. In this method of decontamination, the fluid containing water may be contacted with the chemical composition of the instant invention at pre-configured quantities, to rapidly generate chlorine dioxide in situ, at will, and on-site at controlled rates. In this manner, the chlorine dioxide may be generated at any conceivable concentration for safe use in any desired biological or chemical decontamination application. This method may take advantage of the reactivity of chlorine dioxide precursor and HMS, which occurs quickly at low reagent concentrations without acids, effectors, or catalysts added and may make this method suited for applications requiring rapid reaction to produce aqueous solution or gas phase chlorine dioxide. Alternatively, the decontamination method may comprise a slower, sustained generation of chlorine dioxide.

The decontamination method can be used with an enclosure such as for packaging, particularly when made from polymeric films, which may be impregnated with the dry solid composition. Specifically, the dry reactants HMS and chlorine dioxide precursor can be incorporated into packaging films such as rigid plastic polymers (e.g., polylactic acid (PLA)) or flexible pouch materials. The polymeric material may be configured as a rigid or flexible plastic container to hold water or aqueous solutions (e.g., rigid or collapsible handheld plastic spray-bottles), wherein the dry chemicals may be integrated with the interior surface of the container. Alternatively, the dry solid composition may be impregnated into, contained in, and/or released from a component placed inside the packaging. When the fluid containing water is subsequently added, it can effectuate the dissolution, diffusion, and reaction of the chemicals to generate a chlorine dioxide cleaning and disinfecting solution that can be released or sprayed onto an item. Adding the fluid containing water to chemically impregnated containers in this manner may regulate the dissolution of the dry reagents in water, diffusion of the solvated chemicals through solution, and chemical reaction for controlled production of chlorine dioxide at rates that can be slower than the free aqueous reaction.

The decontamination method can also be used with an enclosure that encompasses at least one item to be decontaminated, wherein the container also contains the dry solid composition and fluid containing water or water vapor is introduced into the container. For example, a polymeric material may be configured as a structured container that holds chemically or biologically contaminated objects (e.g., fresh produce, textiles, uniforms, shoes, equipment, blankets, mats, tents, etc.) that are susceptible to degradation through the growth of molds or spoilage organisms, or that can transmit disease vectors, such as foodborne pathogens. The dry chemicals may be integrated with the interior surface of the container. Alternatively, the dry solid composition may be impregnated into, contained in, and/or released from a component placed inside the packaging container or enclosure. The film may be porous, in which case the hygroscopic properties of HMS may facilitate the gradual absorption of atmospheric water vapor for the consequent dissolution of the dry reagents and subsequent diffusion-reaction to produce chlorine dioxide. Gaseous chlorine dioxide so generated can evolve from the film surface gradually and permeate the interior of the packaging container to effectuate microbial decontamination of the packaging interior or the surfaces of objects contained therein, such as fruits, vegetables, flowers, plants, textiles, or other materials stored in the enclosed space of the packaging container made of polymeric films.

As discussed above, that atmospheric water vapor that triggers the HMS-chlorine dioxide precursor reaction in chemically impregnated plastic containers, packages, or enclosures can be provided by wet or moist contaminated objects (e.g., wet textiles used for clothing, parachutes, shelters or tents) or by humidity-generating products (e.g., transpiring or respiring fresh produce, fruits, vegetables, or berries, plants, or cut flowers) that generate a humid environment inside the containers. Alternatively, the enclosures can have breathable holes such that the enclosure allows the exchange of water vapor between the enclosure interior and exterior atmosphere. In all cases, the chemically-impregnated plastic absorbs water, dissolves the dry reagents, and induces chemical production of chlorine dioxide gas inside the enclosure to kill molds, fungi, bacteria, other microorganisms, or chemical contaminants present.

Since the enclosure may contain fresh produce or plant tissue, the potential for direct contact between the edible foodstuff and the present invention of the HMS-chlorine dioxide precursor chemical reagents or the reaction end-products other than chlorine dioxide may be of understandable concern. Accordingly, as mentioned above, the HMS and chlorine dioxide precursor may be impregnated into, contained in, and/or released from a component rather than the interior surface of the packaging material, thereby separating the dry chemical reagents and end-products from each other and from direct contact with the produce or foodstuff. This item may be, for example, an absorbent hydrogel polymer pad material, such as those commonly used in food packaging containers to absorb water or meat juices. Such an absorbent hydrogel polymer pad may be configured and placed in containers, packages, or enclosed spaces of any size and dimension in humid or humidity-controlled environments for the slow, sustained generation of chlorine dioxide. If the polymeric pad contains superabsorbent hydrogel, it may absorb water or water vapor produced in the packaging container by the active transpiration of the fresh produce, such that the water wicks into the pad, effectuates dissolution of dry chemical reagents, and allows diffusion and reaction to take place. Therefore, such an item can produce chlorine dioxide slowly and sustainably in-container, in-package, in-enclosure, or in any confined space and can be scaled to areas of any size or dimensions.

The contacting step of the above method for decontaminating an item may comprise stimulating a hydrogel in a manner that causes the hydrogel to release or absorb the fluid containing water wherein the composition is positioned to contact the released or absorbed fluid. This can allow the availability of the fluid containing water to be regulated using the stimuli-responsive hydrogel polymer.

By controlling the external stimulus (e.g., temperature, pH, redox potential), the hydrogel polymer can be induced to release bound water and trigger reaction of the dry reagents located externally to the hydrogel polymeric network. Alternatively, an unhydrated hydrogel polymer can contain dry chemical reagents, then be stimulated to absorb water, such that water migrates through the hydrogel and serves as a carrier medium for dissolution, diffusion, and reaction of the dry reagents to produce chlorine dioxide in solution or the gaseous phase.

The hydrogel may be a thermoresponsive hydrogel, which absorbs water at temperatures below its lower critical solubility temperature (LCST) and releases water at temperatures above its LCST. The thermoresponsive hydrogel can be impregnated with or contain dry chemical reagents of HMS and chlorine dioxide precursor in spatially discrete regions, then absorb water at temperatures below its respective LCST, to effectuate production of chlorine dioxide. Conversely, thermoresponsive hydrogel polymers can release water at temperatures above the LCST, to provide an external source of water to the dry reagents and produce chlorine dioxide. The stimuli-responsive hydrogel can be incorporated into a sachet or absorbent pad and added to containers or enclosures that store or contain microbiologically contaminated objects, such as fresh produce, textiles (e.g., uniforms, tents and shelter, parachutes, blankets, and other textiles susceptible to microbial corrosion, automotive vehicles (floor mats, upholstery, carpets, etc.) and the like.

The present disclosure also provides for a method of making a dry solid composition, the method comprising physically arranging a chlorine dioxide precursor and HMS in an anhydrous environment.

The present disclosure provides a composition and methods for convenient production of chlorine dioxide for use in either aqueous or gaseous forms by combining liquid or vaporous water with the dry chemical reagents HMS and a chlorine dioxide precursor. The composition may utilize reagents in the form of dry powders which, when mixed with water, can rapidly produce chlorine dioxide at times and in amounts scalable to any scale, depending on the proportions and initial concentrations of reagents. A composition and methods are provided that allow for chlorine dioxide production rapidly at any concentration or slowly and continuously at low concentrations, preferably as a gas released in a confined space or enclosed area scalable to any size and dimensions, compartment, container, or package holding items to be decontaminated. The water can be used to effectuate dissolution, diffusion, and reaction for the production of chlorine dioxide. In addition to being convenient, this reaction is very safe and does not disturb the environment. The dry reagent chemicals are among the safest in use, and have separate instances of extensive use for many years and in many different contexts.

The water used to dissolve the two reagents and allow them to react can be treated or untreated water, groundwater, or water from other available sources in a field setting. If treated by distillation or ion exchange, it may be favorable if the water is a near-neutral pH. If the treated water is allowed to come into contact with carbon dioxide in the atmosphere, the water may be slightly acidic, having a pH between 5 and 7. This acidity range shows no discernible effect on reaction progress of the instant invention during experimentation. If treated by alkalization, as some municipalities do to precipitate toxic metal ions such as lead(II), the water may be slightly alkaline, having a pH greater than 7. Water so pre-treated also shows no discernible effect on the reaction progress. Untreated water sources may also be used without interfering with the reaction progress. The water used may be preferably between a pH of 4 and 10. Water of pH values outside this range may effectuate the HMS-chlorine dioxide precursor reaction, and may also introduce issues relating to the handling and disposal of the invention for in situ chlorine dioxide generation. The generated chlorine dioxide can disinfect contaminated water to render potable water.

Unused reactants and the end-products of the reaction are known as being environmentally safe and likely will not require specialized handling or disposal methods. The composition of the product mixture may depend on several factors including, especially, the concentrations of the initial reactants, amount and rate of water addition, water quality, and the length of time the reagents are allowed to be in contact together in water. The other end-products of the reaction of the instant invention may include chloride ion, hydrogen ion, sulfate and hydrogen sulfate ions, bicarbonate ions, and carbon dioxide gas.

The compositions and methods described herein can employ chemistry that does not employ the chemistry or methods described in the background section of the present disclosure.

EXAMPLES

Example 1

We placed 80 mL of water in a beaker then added solid sodium chlorite (Technical grade) with stirring to initiate dissolution of the solid. We added solid HMS while stirring, and the reaction between chlorite-HMS occurred immediately (in under 2 seconds) to produce the visually evident yellow color indicative of $ClO_2$ by dissolution and reaction of the solid reagents in water. We measured the results using a $ClO_2$-specific test strip (Chlorine dioxide test strips, low range 0-10 ppm, Selective Micro Technologies, Beverly, Mass.). This process was repeated using higher concentrations of dry reagents and again produced the visually evident yellow color indicative of $ClO_2$ (≥500 ppm) within 10 seconds of mixing the dry reagents (the time includes detection with the Chlorine dioxide test strip, high range 0-500 ppm, Selective Micro Technologies, Beverly, Mass.). Similar chemical tests were used to confirm the production of $ClO_2$ for Experiments 1-9.

Example 2

Microbiological validation of aqueous $ClO_2$ generated by the HMS-chlorite reaction was accomplished using spores of *Bacillus cereus*. The recovery and enumeration of the bacterium was attained using serial dilutions and plate-counting with a Nutrient Agar (NA) medium. An aqueous suspension of *B. cereus* spores was added to 10 mL of sterile water and paddle-blended for 15 minutes, then a minute amount of reductant was added. This control sample yielded plate-counts of approximately $5.5\times10^4$ CFU/mL. Adding the *B. cereus* inoculum to 10 mL of 100 ppm aqueous $ClO_2$ solution generated by the HMS-chlorite reaction, mixed in a paddle-stomacher for 15 min, then adding a minute amount of reductant sufficient to quench the excess $ClO_2$ (solution turned from yellow to clear) yielded no discernible colonies on the NA plates at any dilution ($1\text{-}10^{-6}$). Similar results were obtained with inoculated fabrics. A 10 microliter inoculum of *B. cereus* suspension was spot-inoculated onto a sterile $1\times1$ $in^2$ fabric sample then air-dried in a bio-hood for 25 minutes, this same fabric is used in personal protective garments designed to protect wearers from chemical and biological attacks (e.g., *Bacillus anthracis* spores, a causative agent of 'Anthrax'). We had previously used this procedure to recover *B. anthracis* Sterne spores. The inoculated protective garment fabric was placed in 100 ppm $ClO_2$ solution and mixed with a paddle-blender for 15 min before finally being quenched with reductant. Dilutions of $1\text{-}10^{-6}$ revealed no discernible growth of *B. cereus*. The incubation time used for the NA plates was 18 hours at a temperature of 37° C.

Example 3

Microbiological validation of the reaction chemistry provided by the present disclosure was carried out using military textiles that had gotten wet and exhibited signs of mold growth. Dry reagents of HMS and chlorite ion were added to distilled de-ionized water to produce chlorine dioxide. A cotton-based parachute sleeve that is characteristically used to hold and release parachutes during jumps and to store folded parachutes after jumps was chosen for use. The cotton sleeve exhibited dark spots indicative of potential mold colonies that could degrade the tensile strength of the cotton fibers, although such loss in tensile character was not observed in direct tensile testing of the cotton. Approximately 1×1 in$^2$ was cut from a parachute sleeve and placed using sterile forceps into a Petri dish of sterile Potato Dextrose Agar (PDA) with a few drops of sterile water. Samples were stored at both 25° C. and 30° C. and exhibited mold growth within 3-4 days, the growth in the 30° C. sample being more robust and luxuriant. A 1×1 in$^2$ sample was removed from the moldy dish using a sterile technique and placed in a new sterile Petri dish of PDA with sterile water. A second 1×1 in$^2$ sample was placed in a plastic pouch with 10 mL of 100 ppm $ClO_2$ solution and mixed in a paddle-blender for 2 minutes intermittently over a 20 minute period. At 20 min, reductant was added to quench any excess $ClO_2$, and the sample was placed on a fresh Petri dish of PDA. Both samples were stored at 30° C. for 5 days. The moldy sample exhibited luxuriant mold growth, and the $ClO_2$-treated sample showed no signs of mold growth on the cotton sleeve or on the PDA.

Example 4

Samples of PLA film (16 inches wide, 0.2 mm thickness) were cut into 2 inch square coupons. Saturated solutions of sodium chlorite in water and HMS in water were prepared. Then, using separate Pasteur pipettes for each solution, droplets of concentrated chlorite ion solution were placed onto two PLA squares, and droplets of concentrated HMS were placed onto two other PLA squares, such that the HMS and chlorite ions were spatially segregated. Also droplets of HMS concentrate and chlorite ion concentrate were placed onto spatially discrete regions of a single PLA coupon. All coupons were placed in a glass dish and incubated overnight at 25° C. and dried. A first test included immersing one dry chlorite ion coupon and one dry HMS coupon into 80 mL of water in a beaker at the same time. Rather than the instantaneous visual appearance of yellow $ClO_2$, a 25 second delay elapsed before the solution began to show a faint, pale yellow color. After 3 minutes, a 1 ppm $ClO_2$ solution had formed, and measurements were taken using a chlorine dioxide test strip.

Example 5

The preparation steps detailed in Example 4 were repeated with several samples in 225 mL water. In 30-60 seconds, the solution became the faint yellow color indicative of the presence of $ClO_2$. In about 10-15 min, the solution became pervasively yellow and measured approximately 25 ppm $ClO_2$ with test strips (high range, 0-500 ppm). From these results it was noted that the dissolution-diffusion-reaction introduced a physical technique that effectively slowed the occurrence of chemical reaction between the chlorite and HMS in water.

Example 6

We tested a clamshell package made of plastic (commonly PLA or polyethylene terephthalate (PET)), typical of the packaging used to contain fresh produce or berries as sold in supermarkets, convenience stores, and other grocery stores. These clamshell packages have vent holes that allow the free-flow exchange of gases between the interior of the package and its surrounding environment.

A beaker with two $ClO_2$ indicator test strips (high range, 0-500 ppm), one *Geobacillus stearothermophilus* 7953 autoclave sterility test strip and one *Bacillus atrophaeus* ethylene oxide gas sterility test strip, was placed inside the clamshell package. A piece of blue material comprising non-woven textiles and superabsorbent hydrogel, characteristic of a common disposable diaper, was cut into a 3×1 inch rectangle. Dry sodium chlorite and dry HMS were placed on spatially separate regions of the material. The blue absorbent pad was sprayed with a small amount of water, and then folded in half. The entire clamshell package (containing the indicator strips, microbial test strips, and blue pad with reactive reagents) was placed inside a desiccator charged with saturated salt solution to generate an interior atmosphere of 87% relative humidity (RH) at 25° C. The entire desiccator assembly, containing the salt solution in the bottom and the clamshell package above the solution on a perforated platform, was placed inside an incubator at 35° C., which re-equilibrated and increased RH to 89%. After 24 hours, the $ClO_2$ test strips indicated $ClO_2$ had formed in a concentration of about 25-50 ppm. The indicator test strips for *G. stearothermophilus* and *B. atrophaeus* spores were both negative for microbial growth, confirming that the $ClO_2$ exposure had sterilized these bacterial spores.

This example, therefore confirmed a proof-of-concept for a preferred embodiment of the Compartment-of-Defense (CoD) that is readily adaptable to other types of packaging, containers, or enclosures and scalable to other enclosed areas of different sizes, dimensions, and configurations for myriad applications. Specifically, the test confirmed that the chlorite-HMS reaction had taken place through the absorption of water into the absorbent polymeric pad substrate. The dry reagents in the absorbent polymeric pad, when stored in a humid environment (89% RH) to absorb water vapor, caused dissolution, diffusion, and reaction of the reagents to produce $ClO_2$ in a time-released manner. This embodiment is suitable for fresh fruit, other fresh produce, plants such as flowers, as well as military equipment and textiles (e.g., parachute sleeves, vehicle mats, upholstery, and carpets), all of which, when stored in humid environmental conditions, have the propensity to experience growth of bacterial cells, spores, fungi, molds, mildew, viruses, and bacteriophages.

Example 7

The absorbent polymeric material used in Example 6 above can be taken from a common diaper, sanitary napkin, incontinence undergarment or the like. Such materials are generally constructed to consist of a nonwoven pervious top layer that allows rapid strikethrough with minimal re-wetting, a layer of absorbent material ("fluff") comprising a superabsorbent hydrogel (usually an acrylic acid derivative, or potentially cellulose-based polyelectrolyte hydrogels), and an impervious outer layer. Such materials are also used as an insulator and to absorb and wick any water when biological samples are transported frozen (and from ice that may thaw during shipment or delivery). We envision that dry sodium chlorite and dry HMS could be added to spatially discrete or segregated regions of the fluff or superabsorbent layers of any one of the items discussed above.

We sprayed water onto the top layer of a diaper such that it was absorbed into the diaper's absorbent layers, the water was absorbed and distributed, as would have occurred with urine or other bodily fluid, and effectuated the dissolution, diffusion, and reaction of the dry chlorite ion and dry HMS in the hydrated polymeric medium to produce chlorine dioxide. The presence of chlorine dioxide was confirmed with indicator test strips inserted into the fluff and superabsorbent layers or placed in contact with the top layer. Thus, these results support the present invention being used to safely and controllably generate chlorine dioxide as an anti-microbial or antiseptic in wearable clothing or sanitary garments comprising non-woven or woven textiles. We envision that the chlorine dioxide would help prevent rashes and other types of irritations caused by prolonged contact with enclosed sanitary or other wearable garments, such complications may occur, for example, during prolonged periods in which showering, bathing, laundering, and personal hygiene facilities are of limited availability for protracted durations.

In addition to the non-woven/absorbent materials mentioned above to hold dry reagents and absorb and wick water to produce chlorine dioxide from dry HMS and dry sodium chlorite, we envision other polymeric matrices such as hydrogels, stimuli-responsive hydrogels, or cellulose materials being used to contain dry chemical reagents, absorb moisture, and to drive the chemical production of chlorine dioxide. For example, cellulose is used to make common household sponges that absorb water and can readily effectuate a reaction among dry chemical reagents impregnated in the cellulose material.

We envision additional other polymeric matrices containing these reagents such as stimuli-responsive hydrogels, which can undergo transformations and changes in properties in response to specific stimuli from the external environment, such as temperature, pH, electric fields, and other types of stimuli. Thermoresponsive hydrogels derived from poly-N-isopropylacrylamide, for example, lose water at temperatures above their lower critical solution temperature (LCST) and absorb water at temperatures below their LCST.

To demonstrate examples of this behavior, a thermoresponsive hydrogel polymer was synthesized to consist of poly-N-isopropylacrylamide and chitosan (poly-N-isopropylacrylamide-co-chitosan, LCST≈29.2° C.). Drying the sample overnight in a vacuum oven at 40° C. produced a collapsed, dry hydrogel sample weighing 244.5 mg. After storing that sample in excess water at refrigerator temperatures (4° C.) for 30 minutes, the weight increased to 848.4 mg, indicative of the weight of water absorbed by this hydrogel's polymer network. Moving that same sample to storage at a temperature of 55° C. for 30 minutes induced the loss of water from the hydrogel, and the weight of the hydrogel decreased to 266.3 mg.

As another example of this behavior, thermoresponsive hydrogel polymer poly-{N-isopropylacrylamide-co-Acrylic acid} (LCST≈31.8-33.3° C.) was synthesized. A sample of poly{N-isopropylacrylamide-co-Acrylic acid} weighing 84 mg after drying by storing overnight at 55° C. increased to 435 mg when stored in water at room temperature for 1.5 hours. The number of cycles between moisture absorption and moisture release is generally known to be unlimited. We envision these or other such thermoresponsive hydrogels being configured as a sachet or absorbent pad and inserted into a container or enclosed space to produce anti-microbial chlorine dioxide to decontaminate the surfaces of objects contained therein.

Example 8

A sample of poly-{N-isopropylacrylamide-co-chitosan} hydrogel was tested with the reaction chemistry of the present disclosure by first drying the hydrogel for 3 days at a temperature of 55° C. so that it became devoid of water. The dried hydrogel was placed in a clean, dry beaker with dry HMS reagent solid placed on top of the hydrogel. Chlorite ion solution was added to the beaker such that the level of solution was near the bottom of the hydrogel and the solution was not high enough to allow direct contact of the chlorite ion solution with the HMS crystals on top of the hydrogel. The hydrogel in the beaker was held in the ambient environment to encourage the hydrogel to take up water containing dissolved chlorite ion as aqueous solution in the beaker. Within 20 minutes, the hydrogel absorbed the aqueous chlorite ion solution and expanded. The diffusion of water through the hydrogel effectuated the dissolution of HMS and the chemical reaction between HMS and the chlorite ions to produce chlorine dioxide, this was visually evident based on the formation of a bright yellow color and confirmed with chlorine dioxide-specific test strip analysis. Therefore, it was shown that a hydrogel could be a substitute for the absorbent pad that absorbs and wicks water to induce the HMS-chlorite reaction in containers or enclosures for the CoD.

Example 9

Based on its thermoresponsive properties, we envisioned a hydrogel could also provide a rate-controlled source of water at temperatures below its LCST to effectuate the production of chlorine dioxide through the chemistry of the present invention. A poly-{N-isopropylacrylamide-co-chitosan} hydrogel was synthesized, dried, stored for 3 days at a temperature of 55° C., then rehydrated in water at a temperature of 25° C. for 24 hours. The water-saturated hydrogel was placed in the bottom of a clean, dry beaker. Dry reagents of HMS and sodium chlorite were also placed in segregated regions at the bottom of the beaker such that these solids were not combined or in contact with each other or with the hydrogel sample. The entire beaker was then incubated at a temperature of 55° C. Within 15 minutes, the hydrogel released sufficient water that accumulated in the bottom of the beaker, to effectuate the dissolution, diffusion, and oxidation-reduction chemical reaction of the reagents to produce chlorine dioxide, as visually evident by its yellow color and confirmed with chlorine dioxide test strips (high range, 0-500 ppm).

The above process was repeated using poly-{N-isopropylacrylamide-co-Acrylic acid}. A sample of {N-isopropylacrylamide-co-Acrylic acid} was dried, stored in excess water at room temperature for 1.5 hours, then placed in a clean, dry beaker with spatially segregated dry reagents. During incubation at a temperature of 55° C. for about 20 minutes, the hydrogel released water sufficient to induce the production of chlorine dioxide by chemical reaction of the dry reagents, as confirmed with chlorine dioxide test strips.

The foregoing description was primarily directed to one or more aspects of the composition and methods provided for by the present disclosure. Although some attention has been given to various alternatives within the scope of the disclosure, it is anticipated that one skilled in the art will likely realize additional alternatives that are now apparent from the aspects of the composition and methods provided above. Accordingly, the scope of the present disclosure should be determined from the following claims and not limited by the above description.

The invention claimed is:

1. A method for generating chlorine dioxide, the method comprising:
   a) contacting a dry solid composition comprising a chlorine dioxide precursor and hydroxymethanesulfinic acid monosodium salt dihydrate (HMS) with a fluid containing water, wherein contacting the composition with the fluid produces the chlorine dioxide, wherein the fluid containing water is a liquid, aqueous solution, a gas comprising water vapor, a human secretion, or a combination thereof.

2. The method of claim 1, wherein the fluid is the gas comprising water vapor.

3. The method of claim 2, wherein the method further comprises controlling the humidity of the air in a manner that regulates the production of the chlorine dioxide gas.

4. The method of claim 1, wherein the fluid containing water is the human secretion.

5. The method of claim 1, wherein contacting the composition with the fluid containing water comprises stimulating a hydrogel in a manner that causes the hydrogel to release or absorb the fluid containing water and the composition is positioned to contact the released or absorbed fluid.

6. The method of claim 1, wherein the molar concentration ratio of the chlorine dioxide precursor to the HMS is between 100:1 and 1:100.

7. The method of claim 1, wherein the chlorine dioxide precursor is a chlorite ion salt.

8. The method of claim 7, wherein the chlorine dioxide precursor is sodium chlorite.

9. The method of claim 1, wherein the dry solid composition is in the form of a powder or crystals.

10. A method of decontaminating an item, the method comprising:
    contacting the item with chlorine dioxide produced from a chlorine dioxide precursor, hydroxymethanesulfinic acid monosodium salt dihydrate (HMS), and a fluid containing water, wherein the item is a plant product, a perishable food product, or a combination thereof.

11. The method of claim 10, wherein the fluid containing water is a human secretion.

12. The method of claim 10, wherein the item is the plant product.

13. The method of claim 10, wherein the item is the perishable food product.

14. The method of claim 13, wherein the perishable food product is sealed within a packaging container when contacted with the chlorine dioxide.

15. The method of claim 10, wherein a spray device is used when contacting the item with the chlorine dioxide.

16. The method of claim 10, wherein the method further comprises controlling the amount of the chlorine oxide that contacts the item by adjusting the amount of the fluid containing water.

17. The method of claim 10, wherein the chlorine dioxide precursor is a chlorite ion salt.

18. The method of claim 17, wherein the chlorine dioxide precursor is sodium chlorite.

19. A method for generating chlorine dioxide, the method comprising:
    a) contacting a dry solid composition comprising a chlorine dioxide precursor and hydroxymethanesulfinic acid monosodium salt dihydrate (HMS) with a fluid containing water, wherein contacting the composition with the fluid produces the chlorine dioxide, wherein contacting the composition with the fluid containing water comprises stimulating a hydrogel in a manner that causes the hydrogel to release or absorb the fluid containing water and the composition is positioned to contact the released or absorbed fluid.

* * * * *